(12) United States Patent
Stover

(10) Patent No.: US 8,383,684 B2
(45) Date of Patent: *Feb. 26, 2013

(54) METHODS AND FORMULATIONS FOR TREATING INEFFECTIVE OR DECREASED ESOPHAGAL MOTILITY

(75) Inventor: Robert Carl Stover, Lewis Center, OH (US)

(73) Assignee: Bethanamist LLC, Lewis Center, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/430,266

(22) Filed: Mar. 26, 2012

(65) Prior Publication Data
US 2012/0184610 A1  Jul. 19, 2012

Related U.S. Application Data

(63) Continuation of application No. 12/210,995, filed on Sep. 15, 2008, now Pat. No. 8,143,314.

(60) Provisional application No. 61/039,448, filed on Mar. 26, 2008, provisional application No. 60/972,123, filed on Sep. 13, 2007.

(51) Int. Cl.
*A01N 33/12* (2006.01)

(52) U.S. Cl. ..................................... 514/642

(58) Field of Classification Search ........................ None
See application file for complete search history.

(56) References Cited

U.S. PATENT DOCUMENTS

| | | | |
|---|---|---|---|
| 4,879,303 A * | 11/1989 | Davison et al. ............... | 514/356 |
| 5,149,537 A | 9/1992 | Azria et al. | |
| 5,510,385 A * | 4/1996 | Stroppolo et al. ............ | 514/555 |
| 6,610,667 B1 | 8/2003 | Dettmar et al. | |
| 7,303,768 B2 * | 12/2007 | Yoo ............................... | 424/528 |
| 8,143,314 B1 * | 3/2012 | Stover .......................... | 514/642 |

OTHER PUBLICATIONS

Int. J. of Pharmaceutical Compounding vol. 9 p. 473 (2005).*
Agrawal et al J. Clin. Gastroenterol. vol. 41 p. 366 (Apr. 2007).*
Agrawal et al.; Bethanechol improves smooth muscle function in patients with severe ineffective esophageal motility; J. Clin. Gastroenterol., Apr. 2007; 41(4): 366-70.
Allen et al.; Stability of bethanechol chloride, pyrazinamide, quinidine sulfate, rifampin, and tetracycline hydrochloride in extemporaneously compounded oral liquids; Am. J. Health Syst. Pharm., Sep. 1, 1998; 55(17): 1804-09.
Bazil; Muscarinic Pharmacology: No Need to Memorize; Am. J. Pharm. Ed., vol. 63, Summer 1999.
Unknown; General Search, Compounding Article Search; Int'l. J. Pharm. Compound., Aug. 11, 2007.
Unknown; Bethanechol Monograph, 2007.
Caulfield et al.; International Union of Pharmacology. XVII. Classification of Muscarinic Acetylcholine Receptors; Pharmacological Reviews; The Am. Soc. Pharm. & Exp. Therapeutics, vol. 50, No. 2, 1998.
Unknown; Clinical Pharmacology, Module II, Autonomic & Somatic Nervous Systems, Rev. Oct. 2004.
Ehlert et al.; Contractile Role of M2 and M3 Muscarinic Receptors in Gastrointestinal Smooth Muscle; Life Sciences; vol. 64, Nos. 6/7, pp. 387-394, 1999; Elsevier Science, Inc.
Unknown; Bethanechol 5-mg/ml. Oral Liquid; Int'l. J. Pharm. Comp.; vol. 9, No. 6, Nov./Dec. 2005.
Liwang et al.; Pharmacological discrimination between muscarinic receptor signal transduction cascades with bethanechol chloride; Br. J. Pharm.; (2003) 138, 1259-70; Nature Pub. Group.
Unknown; Methylbaraben; Int'l. J. Pharm. Comp.; vol. 4, No. 3, May/Jun. 2000.
Nazarko; The clinical management of dysphagia in primary care; Br. J. Comm. Nurs.; vol. 13, No. 6, Jun. 2008.
Plaisancie et al.; Effects of neurotransmitters, gut hormones, and inflammatory mediators on mucus discharge in rat colon; Am. J. Physiol. 275 (Gastrointest. Liver Physiol. 38): G1073-84, 1998; The Am. Physiol. Soc.
Schlatter et al.; Bechanechol chloride oral solutions: stability and use in infants; Ann. Pharmacother.; Mar. 1997; 31 (3): 294-6.
Squier et al.; Biology of Oral Mucosa and Esophagus; J. Nat. Cancer Inst. Monographs; No. 29, 2001, pp. 7-15.
Neuhuber et al.; Enteric Co-innervation of Striated Muscle Fibers in the Esophagus: Just a "Hangover"?; The Anatomical Record; 262:41-46 (2001).
Kapila et al.; Relationship Between Swallow Rate and Salivary Flow; Digestive Diseases and Sciences, vol. 29, No. 6 (Jun. 1984), pp. 528-533.
Humphries et al.; Effect of Oral Bethanechol on Parameters of Esophageal Peristalsis; Digestive Diseases and Sciences, vol. 26, No. 2 (Feb. 1981), pp. 129-132.

* cited by examiner

*Primary Examiner* — Sheela J Huff
(74) *Attorney, Agent, or Firm* — Standley Law Group LLP

(57) ABSTRACT

Disclosed embodiments describe pharmaceutical compositions and methods for treating ineffective esophageal motility in which bethanechol and pharmaceutically acceptable absorption enhancers including bile acids and mixtures thereof are topically introduced to the esophagus. Therapeutically effective amounts of bethanechol are delivered while reducing or eliminating parasympathetic nervous system side effects normally associated with systemic bethanechol delivery.

6 Claims, No Drawings

METHODS AND FORMULATIONS FOR TREATING INEFFECTIVE OR DECREASED ESOPHAGAL MOTILITY

CROSS-REFERENCE TO RELATED APPLICATIONS

This application claims the benefit of prior U.S. Provisional Application Nos. 60/972,123, filed Sep. 13, 2007, 61/039,448, filed Mar. 26, 2008, and U.S. Nonprovisional application Ser. No. 12/210,995, filed Sep. 15, 2008, the content of which is hereby incorporated by reference as if recited fully herein.

TECHNICAL FIELD

This description relates generally to the treatment of ineffective or decreased esophageal motility and particularly to methods and formulations comprising bethanechol to enhance the swallowing mechanism.

BACKGROUND

The mechanism of swallowing, also known as deglutition, while generally not given much consideration by healthy individuals, is highly complex and involves the control and coordination of a number of physiologic processes within the body. Initially, food in the mouth is prepared for entry into the esophagus and eventually the stomach and the rest of the gastrointestinal (GI) tract. In the case of solid food, it is chewed, or masticated, and formed into a bolus using the jaw muscles, the teeth, and the tongue. In the case of liquids, the appropriately sized amount of liquid is prepared. Next, the bolus enters the pharynx and subsequently into the esophagus. Peristalsis moves the bolus from the pharynx, through the esophagus, and into the stomach. The swallowing process in the pharynx and the esophagus is coordinated by the autonomic nervous system. Located within the smooth and striated muscle layers of the pharynx and the esophagus are various muscarinic receptors which, although not currently completely understood, when activated, appear to effect peristalsis. These muscarinic receptors help control the smooth and striated muscle layers not only of the esophagus, however, but of the lower gastrointestinal tract, and the bladder. They thus effect peristaltic waves to move materials through the esophagus and the rest of the GI tract and, in the case of the bladder, discharge urine.

Ineffective esophageal motility is associated with many disorders affecting humans. For example, human immunodeficiency virus (HIV) and cancer chemotherapy and radiation patients often have esophageal motility problems related to the disease processes themselves and/or from side effects of treatment. HIV patients, in particular, are currently treated with multi-medication regimens often requiring multiple daily doses. Unfortunately, missing doses of medication can lead to medication resistance in those patients, compromising treatment. In addition, the elderly and patients suffering from strokes or traumatic brain or spinal cord injury, Parkinson's Disease, multiple sclerosis, multiple system atrophy with autonomic phenomena (formerly known as Shy-Drager syndrome), and amyotrophic lateral sclerosis often suffer from ineffective esophageal motility. It has been reported that over one-half of all stroke victims suffer from acute ineffective esophageal motility. It has also been reported that the majority of elderly Parkinson's patients die from bronchial pneumonia and infectious shock and choking is one of the main causes of aspiration pneumonia. Finally, certain drugs can cause such an effect. Examples include antimuscarinics (muscarinic receptor antagonists), including, for example, tolterodine.

Bethanechol, available as 2-carbamoyloxpropyl-trimethyl-amonium chloride, is a parasympathomimetic drug that exerts its effect directly and selectively on the muscarinic M2 receptors and, it is believed, to a certain extent, on the M4 receptors and the M3 receptors and is not inactivated by acetylcholinesterase. See, Liwang L., et at., "Pharmacological discrimination between muscarinic receptor signal transduction cascades with bethanechol chloride." British Journal of Pharmacology, 138 (2003) 1259-70, incorporated herein by reference, Bethanechol has been used for some time for the treatment of urinary retention associated with neurogenic bladder, to stimulate lower gastrointestinal motility, and to help prevent GERD. Formulations of bethanechol consist of either tablets, sublingual tablets, subcutaneous injection, or an oral solution consisting of, for example, bethanechol chloride (5 mg/ml) combined with a suspending vehicle of Ora-Plus® (Paddock Laboratories, Inc., Minneapolis, Minn.) and either Ora-Sweet® (Paddock Labs) or cherry syrup. Recently, in 50 mg oral doses, bethanechol was shown, after 15 and 40 minutes, to improve esophageal motility. See, Agrawal, A., et at., "Bethanechol improves smooth muscle function in patients with severe ineffective esophageal motility." Journal of Clinical Gastroenterology, 41 (4) (2007) 366-70, incorporated herein by reference. All such dosing is designed to be absorbed into the blood stream to be made available to the muscarinic receptors. When provided systemically, however, bethanechol can cause undesirable side effects, including diarrhea, flushing, increased sweating, nausea, stomach pain, or gas, and, importantly, urinary urgency. In the case of HIV and cancer chemotherapy patients, moreover, since nutrient absorption is important in treating these patients, the side effects of diarrhea and abdominal cramping precludes the systemic application of bethanechol for esophageal motility problems in these patients. In fact, there is currently no safe and effective treatment for esophageal motility disorders in these patients. Thus, there exists a need for a formulation and method for effectively treating ineffective esophageal motility while eliminating or reducing undesirable side effects associated with systemic dosing.

SUMMARY

To meet these needs, the present disclosure describes a low-dose bethanechol formulation comprising bethanechol, a pharmaceutically acceptable absorption enhancer such as an ox bile acid mixture, and a pharmaceutically acceptable carrier such as water and a method of treatment for applying the formulation to the pharynx and esophagus. This formulation and method of treatment allows for the topical delivery of a therapeutically effective amount of bethanechol to the muscarinic receptors in the pharynx and esophagus while reducing or eliminating the undesirable side effects associated with traditional bethanechol formulations and methods of delivery for the treatment of ineffective esophageal motility.

In one general aspect, a pharmaceutical composition for the treatment of ineffective esophageal motility is described.

In one embodiment, the composition comprises from about 15 millimolar to about 70 millimolar bethanechol or pharmaceutically acceptable salts thereof; about 500 millimolar to about 700 millimolar one or more pharmaceutically acceptable bile acids; and a pharmaceutically acceptable liquid carrier. In a further embodiment, the concentration of bethanechol is about 25 millimolar. In a further embodiment, the parasympathetic nervous side effects normally associated with the administration of bethanechol are reduced or virtually eliminated.

In a further embodiment, the bile acids comprise taurocholic acid, pharmaceutically acceptable salts thereof, or pharmaceutically acceptable metabolically related derivatives thereof; taurochenodeoxycholic acid, pharmaceutically acceptable salts thereof, or pharmaceutically acceptable metabolically related derivatives thereof; and taurodeoxycholic acid, pharmaceutically acceptable salts thereof, or pharmaceutically acceptable metabolically related derivatives thereof. In a further embodiment, the pharmaceutically acceptable liquid carrier is water.

In a further embodiment, a pharmaceutical composition for the treatment of ineffective esophageal motility is described which composition comprises a pharmaceutically acceptable muscarinic receptor agonist; a pharmaceutically acceptable absorption enhancer; and a pharmaceutically acceptable liquid carrier, wherein the composition is suitable for topical application to the back of the throat, pharynx, or esophagus of a patient in need of treatment; and parasympathetic nervous system side effects normally associated with the muscarinic receptor agonist are reduced or virtually eliminated. In a further embodiment, the muscarinic receptor agonist is selective to M2 receptors. In a further embodiment, the muscarinic receptor agonist is bethanechol.

In a further embodiment, the absorption enhancer comprises a bile acid mix of taurocholic acid, pharmaceutically acceptable salts thereof, or pharmaceutically acceptable metabolically related derivatives thereof; taurochenodeoxycholic acid, pharmaceutically acceptable salts thereof, or pharmaceutically acceptable metabolically related derivatives thereof; and taurodeoxycholic acid, pharmaceutically acceptable salts thereof, or pharmaceutically acceptable metabolically related derivatives thereof. In a further embodiment, the muscarinic receptor agonist is bethanechol and the molar ratio of the bile acid mix to bethanechol is from about 10:1 to about 40:1.

In a further embodiment, the absorption enhancer is chosen from the group consisting of: taurocholic acid, pharmaceutically acceptable salts thereof, or pharmaceutically acceptable metabolically related derivatives thereof; glycocholic acid, pharmaceutically acceptable salts thereof, or pharmaceutically acceptable metabolically related derivatives thereof; glychocholic acid, pharmaceutically acceptable salts thereof, or pharmaceutically acceptable metabolically related derivatives thereof; taurochenodeoxycholic acid, pharmaceutically acceptable salts, or pharmaceutically acceptable metabolically related derivatives thereof; taurodeoxycholic acid, pharmaceutically acceptable salts thereof, or pharmaceutically acceptable metabolically related derivatives thereof; glycochenodeoxycholic acid, pharmaceutically acceptable salts thereof, or pharmaceutically acceptable metabolically related derivatives thereof; ox bile extract; propylene glycol; cholic acid, pharmaceutically acceptable salts thereof, pharmaceutically acceptable metabolically related derivatives thereof, or its monosodium phosphate derivative; deoxycholic acid, pharmaceutically acceptable salts thereof, pharmaceutically acceptable metabolically related derivatives thereof, or its monosodium phosphate derivative; diacetyl tartaric acid esters of (M)mono- and diglycerides or their monosodium phosphate derivatives, glycocholic acid, pharmaceutically acceptable salts thereof, pharmaceutically acceptable metabolically related derivatives thereof, or its monosodium phosphate derivative, mono- and diglycerides or their monosodium phosphate derivatives, and combinations thereof.

In a further embodiment, the absorption enhancer comprises about 500 millimolar bile acids, pharmaceutically acceptable salts thereof, or pharmaceutically acceptable metabolically related derivatives thereof. In a further embodiment, the absorption enhancer is lipophilic and carries a negative charge at mammalian physiological pH ranges. In a further embodiment, the absorption enhancer concentration is about 500 millimolar. In a further embodiment, a method is disclosed for applying a bethanechol, absorption enhancer, liquid carrier composition to the posterior pharynx.

In a further embodiment, the application is spraying, swabbing, squirting, or gargling. In a further embodiment, the muscarinic receptor agonist is bethanechol; the application is spraying and each spray delivers greater than about 0.1 ml but less than about 0.5 ml; and the concentration of bethanechol is between about 3 mg/ml and about 15 mg/ml. In a further embodiment, the concentration of bethanechol is about 5 mg/ml.

In another general aspect, a method of treating a patient suffering from ineffective esophageal motility is described. The method comprises topically applying a therapeutically effective amount to the back of the esophagus of the patient, a composition comprising from about 15 millimolar to about 700 millimolar bethanechol or pharmaceutically acceptable salts thereof; about 500 millimolar one or more pharmaceutically acceptable bile acids; and a pharmaceutically acceptable liquid carrier; and wherein parasympathetic nervous system side effects normally associated with bethanechol are reduced or virtually eliminated.

In a further embodiment, the therapeutically effective amount is between about 3 mg and about 15 mg. In another general aspect, a method is disclosed for facilitating a therapeutic esophageal peristaltic effect to a patient in need of treatment while reducing or virtually eliminating a parasympathetic nervous system side effect. The method comprises topically administering to the esophagus a therapeutically effective amount of bethanechol to facilitate esophageal peristalsis so that the parasympathetic nervous system side effect is reduced while maintaining the therapeutic esophageal peristaltic effect.

In a further embodiment, the therapeutically effective amount of bethanechol is between about 3 mg and about 10 mg. In a further embodiment, the patient in need suffers from acquired immune deficiency syndrome, stroke, amyotrophic lateral sclerosis, acid reflux disease, spinal cord injury, Parkinson's Disease, Alzheimer's Disease, multiple sclerosis, and combinations thereof.

In a further embodiment, a method for improving the absorption of a topical pharmaceutical treatment possessing an active ingredient with a stable ionic charge at physiological pH is described. The method includes the following steps: combining the active ingredient with a complimentary counter-ionic molecule, the counter-ionic molecule comprising a charged moiety for complimenting the charge of the active ingredient and a hydrophobic moiety; and formulating the treatment for application to the gastrointestinal tract.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

DETAILED DESCRIPTION

Bethanechol is known to be poorly absorbed by the mucosal lining of the gastrointestinal tract. It is a stable, water-soluble molecule, but has a positive charge on a quaternary amine which hampers its absorption. Thus, to achieve the beneficial effects of bethanechol on esophageal motility, systemic dosages in the range of 25-50 mg are required. Further, absorption of bethanechol at these dosage levels by the stomach and lower GI tract results in systemic distribution to other areas of the body such as the urinary tract and colon. A 50 mg oral dosage, for example, is believed to be about 22 percent absorbed in the stomach and intestines, which are rich in blood supply. This would result in a systemic level of about 11 mg of bethanechol. As described herein, however, bethanechol delivered locally to the pharynx and esophagus in a form that can more easily be absorbed by the mucosal lining of the pharynx and esophagus and delivered to the muscarinic receptors, principally the M2 receptors, can provide esophageal motility benefits, as well as increased salivation, while minimizing or avoiding systemic absorption and reducing or eliminating undesirable side effects. Enhancing the reduction or elimination of undesirable side effects is the fact that the esophagus has low vascularization, thus inhibiting the systemic absorption of bethanechol.

As used herein, by "pharmaceutically acceptable" it is meant the named ingredient must be compatible with the other ingredients of the formulation, and not deleterious to the recipient thereof.

As used herein, by "therapeutically effective amount" it is meant an amount which provides a therapeutic benefit in the treatment, management, or prevention of conditions that are responsive to the named compound. A pharmaceutically acceptable absorption enhancer can help provide a mechanism whereby the bethanechol is delivered to the esophageal mucosa M2 receptors and to the M2 receptors in the underlying deeper smooth and striated muscles. Included are those absorption enhancers which are lipophilic and carry a negative charge at mammalian physiological pH ranges (5-8). A member of the bile acid group, of which taurocholic acid is exemplary, allows for enhanced absorption of bethanechol by forming an ionic bond with bethanechol at the negative charge of the bile acid (e.g., the sulfate group of taurocholic acid), thereby carrying bethanechol chloride with it. It is also believed that a member of the bile acid group, of which taurocholic acid is exemplary, acts upon the M3 receptors to alleviate or ameliorate the swallowing dysfunction which is often associated with inflammation. In addition to taurocholic acid, bile acids include, but are not limited to, cholic acid, desoxycholic acid, glycocholic acid, and ox bile extract. Special Bile Acid Mix (New Zealand Pharmaceuticals Ltd., Palmerston North, North Island, NZ) has, for example, the following composition:

| | |
|---|---|
| taurocholic acid | 35.8 wt. percent |
| glycocholic acid | 24.8 wt. percent |
| taurochenodeoxycholic acid | 2.0 wt. percent |
| taurodeoxycholic acid | 9.5 wt. percent |
| glycochenodeoxycholic acid | 1.3 wt. percent |
| glycodeoxycholic acid | 5.0 wt. percent |

Other agents include diacetyl tartaric esters of (M)mono- and diglycerides; mono- and diglycerides; monosodium phosphate derivatives of cholic acid; desoxycholic acid; diacetyl tartaric acid esters of (M)mono- and diglycerides, glycocholic acid, and mono- and diglycerides; and propylene glycol.

Without attempting to be all-inclusive, absorption enhancers may be chosen from the following group: ox bile; taurocholic acid, pharmaceutically acceptable salts thereof, or pharmaceutically acceptable metabolically related derivatives thereof; glycocholic acid, pharmaceutically acceptable salts thereof, or pharmaceutically acceptable metabolically related derivatives thereof; glycocholic acid, pharmaceutically acceptable salts thereof, or pharmaceutically acceptable metabolically related derivatives thereof; taurochenodeoxycholic acid, pharmaceutically acceptable salts, or pharmaceutically acceptable metabolically related derivatives thereof; taurodeoxycholic acid, pharmaceutically acceptable salts thereof, or pharmaceutically acceptable metabolically related derivatives thereof; glycochenodeoxycholic acid, pharmaceutically acceptable salts thereof, or pharmaceutically acceptable metabolically related derivatives thereof; ox bile extract; propylene glycol; cholic acid, pharmaceutically acceptable salts thereof, pharmaceutically acceptable metabolically related derivatives thereof, or its monosodium phosphate derivative; deoxycholic acid, pharmaceutically acceptable salts thereof, pharmaceutically acceptable metabolically related derivatives thereof, or its monosodium phosphate derivative; diacetyl tartaric acid esters of (M)mono- and diglycerides or their monosodium phosphate derivatives, glycocholic acid, pharmaceutically acceptable salts thereof, pharmaceutically acceptable metabolically related derivatives thereof, or its monosodium phosphate derivative, mono- and diglycerides or their monosodium phosphate derivatives, and combinations thereof.

Adding pharmaceutically acceptable thickening agents and viscosity enhancers will also increase the viscosity of the formulation which will act to increase adherence to the esophageal mucosa, and, thus increase contact time. This increased contact time, along with the presence of absorption enhancers will facilitate absorption of bethanechol.

Adding pharmaceutically acceptable flavorings, sweetening enhancers, and bitterness suppressors such as those offered by FlavorX, Inc. (Columbia, Md.) can make the formulation more palatable, and, thus, more likely to be used. Pharmaceutically acceptable antioxidants and antimicrobials can also be added.

It is believed that, as a result of activation of the M2 receptors, pressure within the upper esophagus will increase, initiating a peristaltic wave in the upper esophagus moving toward the LES. The formulation will continue to flow by gravitational forces and dissolution in saliva to the LES, where M2 receptors in the LES will be activated by bethanechol to increase pressure of the LES, helping to prevent reflux of gastric contents back into the esophagus. An exemplary formulation may be prepared by combining between 360 and 900 mg bethanechol chloride, about 600 mg of sodium carboxymethylcellulose or about 240 mg of methylparaben, about 24 mg of glycerin, an absorption enhancer, and preserved water quantum 20 sufficiat to 120 ml total volume of the formulation. Such formulation is suitable for topical spray application to the pharynx and esophagus.

In one general aspect, the composition is effective for treating a patient suffering from ineffective esophageal motility and comprises from about 15 millimolar to about 70 millimolar bethanechol or pharmaceutically acceptable salts thereof, about 500 millimolar one or more pharmaceutically acceptable bile acids, and a pharmaceutically acceptable liquid carrier.

An exemplary formulation comprises 25 millimolar bethanechol, 500 millimolar Special Bile Acid Mix, and sufficient viscosity enhancers in an aqueous solution. In a further exemplary formulation, the molar concentration of taurocholic acid and taurodeoxycholic acid is present in a ratio of about 10:1 to about 40:1 with the molar concentration of bethanechol. Such formulation is suitable for topical spray application to the pharynx and esophagus. The 40:1 ratio balances the need to have an excess of absorption enhancers relative to the bethanechol with cost. The higher the ratio, the less bethanechol that would be required to achieve similar absorption.

An exemplary method comprises treating ineffective esophageal motility while reducing or virtually eliminating an undesirable side effect, particularly a parasympathetic nervous system side effect, in a mammal in need of treatment by topically administering to the pharynx and esophagus of the mammal a therapeutically effective amount of bethanechol and an absorption enhancer to facilitate esophageal peristalsis so that the undesirable side effect, particularly the parasympathetic nervous system side effect, is reduced while maintaining the therapeutic esophageal peristaltic effect. A further exemplary method comprises delivering an amount of bethanechol of between about 3 mg and about 15 mg. A further exemplary method comprises introducing about ten 0.1 ml sprays comprising 5 mg bethanechol per ml and an absorption enhancer. Of the total 5 mg introduced, it is expected about 25 percent of the bethanechol, or about 1.25 mg, is adsorbed. The remaining 3.75 mg would proceed into the stomach and intestines, and, at about a 22 percent absorption rate would result in only about 0.8 mg bethanechol being systemically adsorbed, far below the threshold necessary to produce undesirable side effects.

In one general aspect, delivery is effected by methods effective to introduce the composition to the back of the throat, pharynx, and/or esophagus such that the composition topically contacts the tissues thereof. Examples include a pump spray, for example, a pump spray comprising an extension tube which facilitates delivery deep into the back of the throat. In another general aspect the composition is squirted as a stream or partial stream into the back of the throat. In a further general aspect, the composition is swabbed into the back of the throat. In a further embodiment, the composition is gargled in the back of the throat.

EXAMPLES

A formulation was prepared consisting essentially of 600 mg bethanechol chloride; 600 mg sodium carboxymethylcellulose; 24 ml glycerin; and 29.5 g Special Bile Acid Mix, the Special Bile Acid Mix consisting essentially of 35.8 wt. percent taurocholic acid, 24.8 wt. percent glycocholic acid, 2.0 wt. percent taurochenodeoxycholic acid, 9.5 wt. percent taurodeoxycholic acid, 1.3 wt. percent glycochenodeoxycholic acid, and 5.0 wt. percent glycodeoxycholic acid; mixed in preserved water quantum sufficiat 120 ml total volume of formulation.

On three separate occasions, a healthy male volunteer introduced 10 about 0.1 ml sprays of the above formulation to the back of his throat. After about 10 minutes, the volunteer reported easier swallowing and increased salivation. These effects continued for approximately 90 minutes. At no time during the test did the volunteer experience any undesirable side effects and, particularly, no side effects commonly associated with the administration of high systemic doses of bethanechol.

On five separate occasions, a second healthy male volunteer also introduced 10 about 0.1 ml sprays of the above formulation to the back of his throat. As with the first volunteer, after about 10 minutes, the second volunteer also reported easier swallowing and increased salivation that continued for about 90 minutes. Also as with the first volunteer, at no time during the test did the second volunteer experience any undesirable side effects and, particularly, no side effects commonly associated with the administration of high systemic doses of bethanechol. Neither volunteer experienced any long-term effects.

Ultra manometry was performed on 5 patients employing a 5 mg/ml formulation. The patients were given ten 5 ml swallows of water and then administered the formulation to the back of the throat. After allowing 10 minutes for absorption, the patients were then given another ten 5 ml swallows. None of the patients experienced undesirable parasympathetic nervous system side effects. The data is summarized in the following table:

|  | peristaltic % | normal % | Hypo % | Failed % | Simultan % | Amp 3 mmHG | Amp 7 mmHg |
|---|---|---|---|---|---|---|---|
| 1 pre-test | 0 | 0 | 0 | 94 | 6 | 31.9 | 29.6 |
| 2 pre-test | 10 | 0 | 10 | 10 | 80 | 30.7 | 31.1 |
| 3 pre-test | 70 | 30 | 40 | 30 | 0 | 49.3 | 53.4 |
| 4 pre-test | 30 | 0 | 30 | 60 | 10 | 23.1 | 34.8 |
| 5 pre-test | 30 | 0 | 30 | 70 | 0 | 29.4 | 16.5 |
| 1 post-test | 57 | 0 | 57 | 36 | 7 | 77.7 | 55.6 |
| 2 post-test | 69 | 0 | 69 | 31 | 0 | 26.9 | 29.1 |
| 3 post-test | 90 | 10 | 80 | 0 | 10 | 46.4 | 43.4 |
| 4 post-test | 70 | 0 | 70 | 30 | 0 | 35.2 | 30.7 |
| 5 post-test | 50 | 0 | 50 | 50 | 0 | 32.1 | 12.9 |

|  | Amp 11 mmHg | mean 3/7 mmHg | DCI | CFV cm/sec | Vel 11-3 cm/s |
|---|---|---|---|---|---|
| 1 pre-test | 29.1 | 30.8 | 106.4 |  |  |
| 2 pre-test | 27.8 | 31 | 129.5 | 5.72 | 19.3 |
| 3 pre-test | 49.9 | 51.7 | 302.2 | 2 | 2.5 |
| 4 pre-test | 25.3 | 28.9 | 225.1 | 4.1 | 4 |
| 5 pre-test | 27.3 | 22.9 | 128.1 | 3 | 4.1 |
| 1 post-test | 35.5 |  | 622.4 | 4.8 | 6.4 |
| 2 post-test | 30.8 | 28 | 85.1 | 3.7 | 3.4 |
| 3 post-test | 19.1 | 44.9 | 256.6 | 2.9 | 2.6 |
| 4 post-test | 26 | 32.9 | 297.5 | 2.9 | 3.8 |
| 5 post-test | 22.7 | 22.5 | 100 | 2.4 | 2.3 |

A formulation was prepared comprising 1200 mg bethanechol chloride; 600 mg sodium carboxymethylcellulose; 24 ml glycerine; and 36.9 g Special Bile Acid Mix; mixed in preserved water quantum sufficiat 120 ml total volume of formulation.

The terms "a" and "an" and "the" and similar references used in the context of describing the disclosed embodiments (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosed embodiments and does not pose a limitation on the scope of the disclosed embodiments unless otherwise claimed. No language in the specification should be construed as indicating any non-claimed element essential to the practice of the disclosed embodiments or any variants thereof.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability Preferred embodiments of this invention are described herein, including the best mode known to the inventors for carrying out the invention(s). Of course, variations on the disclosed embodiments will become apparent to those of ordinary skill in the art upon reading the foregoing description. The inventors expect skilled artisans to employ such variations as appropriate, and the inventors intend for the invention(s) to be practiced otherwise than specifically described herein. Accordingly, this disclosure includes all modifications and equivalents of the subject matter recited in the claims appended hereto as permitted by applicable law. Moreover, any combination of the above described elements in all possible variations thereof is encompassed by the disclosed embodiments unless otherwise indicated herein or otherwise clearly contradicted by context.

Having shown and described an embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

This detailed description is intended principally as a description of the present embodiments of the invention, and is not intended to represent the only form in which the present invention may be synthesized, formed, or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A pharmaceutical composition for the treatment of ineffective esophageal motility, comprising:
    a M2 selective, pharmaceutically acceptable muscarinic receptor agonist;
    a pharmaceutically acceptable hydrophobic absorption enhancer; and
    a pharmaceutically acceptable liquid carrier,
wherein:
    the composition is suitable for topical application to the back of the throat, pharynx, or esophagus of a patient in need of treatment; and
    parasympathetic nervous system side effects normally associated with the muscarinic receptor agonist are reduced or virtually eliminated.

2. The composition of claim 1, wherein the muscarinic receptor agonist is bethanechol.

3. The composition of claim 1, wherein the hydrophobic absorption enhancer comprises a bile acid mix comprising:
    taurocholic acid, pharmaceutically acceptable salts thereof, or pharmaceutically acceptable metabolically related derivatives thereof;
    taurochenodeoxycholic acid, pharmaceutically acceptable salts thereof, or pharmaceutically acceptable metabolically related derivatives thereof; and taurodeoxycholic acid, pharmaceutically acceptable salts thereof, or pharmaceutically acceptable metabolically related derivatives thereof.

4. The composition of claim 1, wherein the absorption enhancer is chosen from the group consisting of:
    taurocholic acid, pharmaceutically acceptable salts thereof, or pharmaceutically acceptable metabolically related derivatives thereof;
    glycocholic acid, pharmaceutically acceptable salts thereof, or pharmaceutically acceptable metabolically related derivatives thereof;
    glycochocholic acid, pharmaceutically acceptable salts thereof, or pharmaceutically acceptable metabolically related derivatives thereof;
    taurochenodeoxycholic acid, pharmaceutically acceptable salts, or pharmaceutically acceptable metabolically related derivatives thereof;
    taurodeoxycholic acid, pharmaceutically acceptable salts thereof, or pharmaceutically acceptable metabolically related derivatives thereof;
    glycochenodeoxycholic acid, pharmaceutically acceptable salts thereof, or pharmaceutically acceptable metabolically related derivatives thereof;
    ox bile extract;
    propylene glycol;
    cholic acid, pharmaceutically acceptable salts thereof, pharmaceutically acceptable metabolically related derivatives thereof, or its monosodium phosphate derivative;
    deoxycholic acid, pharmaceutically acceptable salts thereof, pharmaceutically acceptable metabolically related derivatives thereof, or its monosodium phosphate derivative;
    diacetyl tartaric acid esters of (M)mono- and diglycerides or their monosodium phosphate derivatives, glycocholic acid, pharmaceutically acceptable salts thereof, pharmaceutically acceptable metabolically related derivatives thereof, or its monosodium phosphate derivative, monoand diglycerides or their monosodium phosphate derivatives, and combinations thereof.

5. The composition of claim 2, wherein the absorption enhancer is lipophilic and carries a negative charge at mammalian physiological pH ranges.

6. The composition of claim 5, wherein the absorption enhancer concentration is about 500 millimolar.

* * * * *